US005461042A

United States Patent [19]
Loria

[11] Patent Number: 5,461,042
[45] Date of Patent: * Oct. 24, 1995

[54] REGULATION OF THE IMMUNE SYSTEM

[76] Inventor: Roger M. Loria, 3219 Brook Rd., Richmond, Va. 23227

[ * ] Notice: The portion of the term of this patent subsequent to Jan. 11, 2011 has been disclaimed.

[21] Appl. No.: 176,234

[22] Filed: Jan. 3, 1994

Related U.S. Application Data

[63] Continuation-in-part of Ser. No. 95,431, Jul. 23, 1993, abandoned, and a continuation-in-part of Ser. No. 917,720, Jul. 24, 1992, Pat. No. 5,277,907, each, is a continuation of Ser. No. 685,078, Apr. 15, 1991, abandoned, which is a continuation-in-part of Ser. No. 437,903, Nov. 17, 1989, abandoned, which is a continuation-in-part of Ser. No. 291,969, Dec. 30, 1988, Pat. No. 5,077,284.

[51] Int. Cl.$^6$ ..................................................... A61K 31/56
[52] U.S. Cl. ........................... 514/182; 514/953; 514/962
[58] Field of Search ..................................... 514/182, 169, 514/170, 962, 953; 552/583, 606, 615, 634, 636

[56] References Cited

U.S. PATENT DOCUMENTS

| 2,170,124 | 6/1939 | Butenandt et al. | 552/583 |
|---|---|---|---|
| 2,521,586 | 9/1950 | Levy et al. | 552/636 |
| 4,279,532 | 8/1990 | El-Rashidy | 424/448 |
| 4,435,327 | 3/1984 | Petzoldt et al. | 552/636 |
| 5,077,284 | 12/1991 | Loria et al. | 514/171 |
| 5,206,008 | 4/1993 | Loria | 424/45 |
| 5,277,907 | 1/1994 | Loria | 424/93 V |

OTHER PUBLICATIONS

Butenandt, et al, *Ber.*, (1938) 1316–1322.

*Primary Examiner*—Raymond Henley, III
*Assistant Examiner*—K. Weddington
*Attorney, Agent, or Firm*—Glenna Hendricks; Stephen Gates

[57] ABSTRACT

The present invention provides an improved compositions and methods for regulating the immune response, for ameliorating effects of stress, and for avoiding untoward effects of chemotherapy or exposure to irradiation by administration of androstenediol (AED) and androstenetriol (AET). The improved means of regulating immune response can be utilized in treating infectious diseases and immune diseases such as diabetes and chronic fatigue syndrome, both diseases now considered to be immune response related syndromes.

16 Claims, No Drawings

REGULATION OF THE IMMUNE SYSTEM

This application is a continuation-in-part of U.S. Ser. No. 08/095,431, filed Jul. 23, 1993, now abandoned, and of U.S. Ser. No. 07/917,720, filed Jul. 24, 1992 now U.S. Pat. No. 5,277,907, both of which are continuations of U.S. Ser. No. 07/685,078, filed Apr. 15, 1991 now abandoned, which is a continuation-in-part of U.S. Ser. No. 07/437,903 filed Nov. 17, 1989, now abandoned, which is a continuation-in-part of U.S. Ser. No. 07/291,969 filed Dec. 30, 1988, now U.S. Pat. No. 5,077,284.

FIELD OF THE INVENTION

The present invention provides an improved means for regulating the immune response, for ameliorating effects of stress, and for avoiding untoward effects of chemotherapy or exposure to irradiation by administration of androstenediol (AED) and androstenetriol (AET). The improved means of regulating immune response can be utilized in treating infectious diseases and immune diseases such as diabetes and chronic fatigue syndrome, both diseases now considered to be immune response related syndromes.

BACKGROUND OF THE INVENTION

In vertebrates the development of host protection against pathogens requires a selective host immune response that involves the mobilization of the humoral and/or cellular mediated immune responses. Several factors adversely affect the body's protective response capability by causing prolonged immuno-suppression or "down-regulation" of the immune system. It is, in reality, more appropriate to speak of "mal-regulation" or "deregulation" of the immune system than of "down-regulation" since the result is a failure to protect the body from assault. Immuno-suppression provides an opportunity for pathogens to grow in the host. It does not matter what causes the primary insult to immunity. The resulting inability to muster the appropriate immune response has the same effect. Among the many different causes of immuno-suppression are viral, bacterial, fungal, yeast and parasitic infections, chemotherapy, irradiation, severe stress, chronic fatigue syndrome, diabetes mellitus and some forms of steroid therapy.

It has long been known that patients receiving steroid hormones of adrenocortical origin at pharmacologically appropriate doses show increased incidence of infectious disease. A. S. Fauci, *immunolo.rev.* 65, 133–155 (1982); and J. E. Parillo and A. S. Fauci, *Annual Review of Pharmacology and Toxicology* 19, 179–201 (1979). Dehydroepiandrosterone, also known as 3-β-hydroxyandrost-5-en-17-one or dehydroiso-androsterone (referred to hereinafter as DHEA), is a 17-ketosteroid which is quantitatively one of the major adrenocortical steroid hormones found in mammals. M. E. Windholz, *The Merck Index*, Ninth Edition (1976); K. Diem and C. Lentner, *Geigy Scientific Tables* (1975). (Although DHEA appears to serve as an intermediary in gonadal steroid synthesis, the primary physiological function of DHEA has not been fully understood. It has been known, however, that levels of this hormone begin to decline in the second decade of life, reaching 5% of the original level in the elderly.)

Clinically, DHEA has been used systemically and/or topically for treating patients suffering from psoriasis, gout, hyperlipemia, and in has been administered to post-coronary patients. W. Regelson et al., *New York Academy of Sciences* 518, 260–273 (1988). In mammals DHEA has been shown to have weight optimizing and anticarcinogenic effects.

DHEA has been used clinically in Europe in conjunction with estrogen as an agent to reverse menopausal symptoms and also has been used in the treatment of manic depression, schizophrenia, and Alzheimer's disease. DHEA has also been used clinically at 40 mg/kg/day in the treatment of advanced cancer and multiple sclerosis. (Regelson, supra) Mild androgenic effects, hirsutism, and increased libido were the side effects observed. These side effects can be overcome by monitoring the dose and/or by using analogues.

U.S. Pat. No. 5,077,284 entitled "Use of Dehydroepiandrosterone to Improve Immune Response" describes the subcutaneous or oral administration of DHEA to improve the host's response to infections. U.S. Pat. No. 4,978,532 describes use of patch technology to deliver DHEA.

It is now disclosed that DHEA is a precursor in a metabolic pathway which ultimately leads to more powerful agents that increase immune response in mammals. That is, DHEA acts as a biphasic compound: it acts as an immunomodulator when converted to androstenediol (5-androstene, 3β,17β diol hereinafter referred to as βAED) or androstenetriol (5 androstene 3β,7β,17β triol hereinafter referred to as βAET), but in vitro has a certain lymphotoxic and suppressive effect on cell proliferation prior to its conversion to βAED and/or βAET. It is, therefore, now understood that administration of DHEA shows superior immunity enhancing properties as a result of its partial conversion to a more active metabolite.

An agent that would advance the protective regulation of the immune system without giving rise to undesirable side effects seen with DHEA administration would provide particularly advantageous improvement of host resistance against infection. Protective regulation of the immune system could then be effected using lower doses of the chemotherapeutic agent, and would provide more immediate response with a wider range of protection.

DESCRIPTION OF THE INVENTION

The present invention provides compounds and compositions useful for enhancing the protective response of the immune system against infections. The medicinal compositions of the invention are also useful for treating other complications often accompanying immune suppression. The enhancement of the protective immune response may also be referred to herein as up-regulation or regulation of immune response.

The present invention provides means of synthesizing both α and β sterio isomers of AET. Both isomers are present in the body. However, since the activity of the isomers varies, it is important that means of making the separate isomers be provided. It is now known that the βAET is the active agent in regulation of immune response. It is, however, probable that the αAET, when in excess, is in equilibrium with βAET. However, because it is not known at this time what the response delay interval is, the βAET is the composition that is the isomer used therapeutically.

Using βAED and βAET and protected analogues avoids certain side effects resulting from use of DHEA. The use of βAED and βAET avoids many of the androgenic side effects that occur when the precursor DHEA is administered. With βAED and βAET it is possible to obtain rapid, controlled enhancement of immune response. Furthermore, as shown by the information below in Table 1, the βAED is unexpectedly superior to DHEA for purposes of protecting against viral assault since the protection offered differs both quantitatively and qualitatively from protection effected by DHEA. The structures of βAED and the α and β isomers of AET are given below:

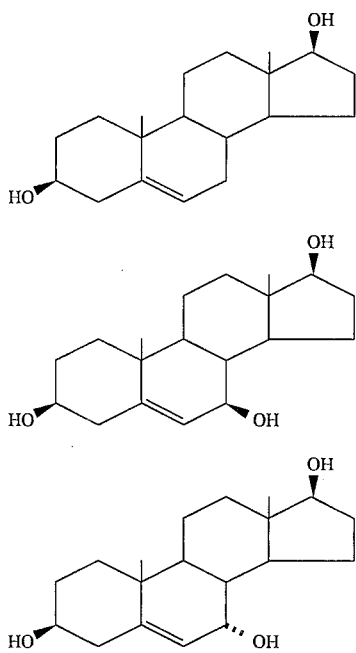

In addition to the medicinal compositions, the invention encompasses analogues and derivatives of βAED and βAET. As indicated later in the exemplification of synthetic techniques, some of the substituted compounds are useful as starting materials or intermediates in making βAED and βAET. βAED is available from commercial sources and has been used as a raw material for production of other steroids. (See U.S. Pat. No. 2,521,586.) The product used in testing was obtained from Sigma. βAED and βAET may also be substituted with protective groups which, on hydrolysis yield βAED or βAET. Hence, acylated and alkylated derivatives are useful as precursors to the βAED and βAET. Compounds such as those of the formula:

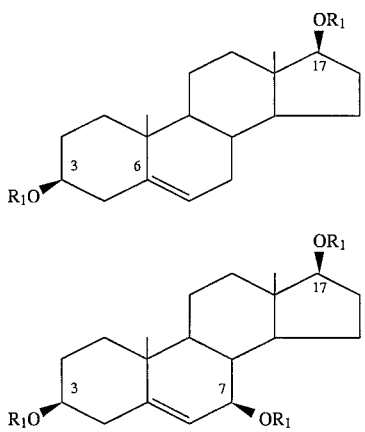

wherein $R_1$ may be H, alkenyl of 2–8 carbons, alkyl of 1–8 carbons, phenylalkyl of 1–4 carbons, phenyl or $COR_2$, wherein $R_2$ is H; alkyl of 1–8 carbons, alkenyl of 2–8 carbons, phenylalkyl wherein the alkyl has 1–4 carbons (including benzyl) or phenyl. Any phenyl moiety may have up to three substituents chosen from among hydroxy, carboxy of 1–4 carbons, halo, alkoxy of 1–4 carbons, alkyl of 1–4 carbons, or alkenyl of 2–4 carbons and wherein any alkyl may be a straight chain, branched chain, or the alkyl may be wholly or partially cyclized.

The acute virus infection used as a model in the examples was chosen because of its widespread effects and the severity of the model to show protection. The Coxsackievirus B4 is lethal to mice. In man, Coxsackie- viruses cause such varied pathologies as upper respiratory infection, pharyngitis, hemorrhagic conjunctivitis, meningitis, exanthem, encephalitis, hepatitis, infantile diarrhea, paralysis, pericarditis, and myocarditis. It is now believed that viruses of this group also have a role in the onset of juvenile diabetes.

The use of βAED and βAET and protected analogues as taught herein provides high levels of protection to vertebrates, including humans, against morbidity arising from infections or exposure to immune suppressive influences. In clinical medicine, treatment with βAED and βAET can lower morbidity in patients exposed to pathogenic organisms. These agents can be effectively used prophylactically in patients known to be particularly susceptible to infection. Patients undergoing surgery or chemotherapy or patients suffering from burns, hypoplastic or aplastic anemias, or diabetes are such susceptible patients who would benefit from prophylactic administration of βAED and/or βAET. Also among the causes of immuno-suppression are viral, bacterial, fungal, yeast and parasitic infections, chemotherapy, irradiation, severe stress, chronic fatigue syndrome and some forms of steroid therapy. The compositions of the invention are particularly useful for treating patients suffering from infections caused by viruses that destroy the body's immune response, such as human immunodeficiency virus (HIV) and hepatitis.

Both βAED and βAET are most efficiently formulated using lipophilic carriers such as DMSO. For subcutaneous administration to animals used in the examples, the active agents were dissolved 1:1 DMSO/ethanol, then diluted for subcutaneous administration to the animals. When the compositions were administered by mouth, they were added to chow to provide a composition containing 0.4% AED. For application to the skin, the AED may, for example, be dissolved in carrier material containing DMSO and alcohol, then applied to a patch. In such instances, the AED in solution may be added to another carrier such as glycerol before application of the composition to the support material of the patch. For vaginal or rectal administration, the AED may be administered by suppository, enema, or by application of creams, etc. Compositions of the invention may be administered by any method that will result in contact of the active agent with tissue of ectodermal origin. Such methods include subcutaneous or intradermal injection or topical application. One means of topical application is the use of skin patches impregnated with the active agent. This means of delivery is advantageous since it is non-invasive and easily administered by relatively unskilled care providers. Compositions of the invention can also be used in veterinary medicine to prevent morbidity that occurs during stress of shipping. Administration of βAED and βAET can be effective as a means to prevent spread of infectious disease and introduction of infectious organisms into the foods for human consumption. βAED and βAET can be administered by subcutaneous injection, in food or drink, by patches applied to the skin, or by inhalation. A particular health concern is the spread of infection through eggs. Eggs are frequently infected during development in the hen. Compositions containing active agents of the invention may be added to the feed or water to prevent bacterial infection in the eggs.

When patches are used on animals or birds the skin should be exposed directly to the patch. When a patch is used, it may be necessary to pluck or shave the bird or animal to expose the skin.

Other preferred methods of administration include buccal, sublingual, nasal or endotracheal routes. Sprays may be useful for this purpose. For nasal administration, the active agent may be delivered as a powder that is snorted. Inclusion complexes such as cyclodextrin inclusion complexes are appropriate compositions for administration to the oralpharyngeal and nasal mucosa.

βAED and βAET may also be given with vaccines to enhance immune response. These agents may be administered either in a composition containing the vaccine or may be given in a composition separate from the vaccine.

The compounds of the invention may also be administered to the intestinal mucosa by oral or rectal routes. Suppositories, solutions for use as retention enemas, and creams or jellies are appropriate carriers for use in rectal administration.

Compounds of the invention may be applied to the vaginal mucosa using creams, jellies, suppositories, or douching solutions. In order to enhance immune response at the site of exposure to infectious organisms, the compounds may be added to prophylactic vaginal preparations or may be used as lubricants on condoms.

Administration of compositions of the invention has proven to be highly effective as a means of protecting against encephalitis and meningitis. The compositions of the invention may be administered intrathecally either at the spinal level or into the cisterna magna.

Active agents of the invention may be administered via ocular route using compositions in the form of drops, creams, or gel solutions or suspensions adapted for ocular application.

βAED and βAET inhibit the adherence properties of body cells. For purposes of effecting the anti-adherence properties of the active agents of the invention may be delivered directly to the epithelial tissue during surgery. An example of such use would involve the application of compositions containing the active agents of the invention to the omentum in conditions such as infection, endometritis and malignancies of the bowel and ovary wherein adherence of foreign cells or particles to normal cells of the peritoneal lining is a problem. Compositions of the invention could, for example, be administered as mists or sprays.

It has now been shown in vivo that DHEA is converted to the βAED and both isomers of AET. The βAED and βAET then act as regulators of the immune response. In the skin, the conversion of DHEA to AED and subsequently to AET appears to be one of the metabolic pathways of DHEA. The human skin has the enzymatic machinery to form 7β-OH DHEA and to cause 7β hydroxylation of AED to yield βAET, while the human adrenal cortex and liver can form only 7α-hydroxylation of DHEA, but not 7β-hydroxylation. The following table indicates the metabolic pathways of DHEA.

| | Trivial or common name | systematic name |
|---|---|---|
| (a) | Dehydroepiandrosterone | (DHEA) 3β-Hydroxy-5-androsten-17-one |
| (b) | Dehydroepiandrosterone sulfate | (DHEAS) 3β-Hydroxy 5 androsten-17-one-sulfate |
| (c) | 7 β-OH Dehydroepiandrosterone | — |
| d) | Androstenediol | (AED) 5-androstene3β, 17β, diol |
| e) | Androstenetriol | (AET) 5-androstene-3β, 7β, 17β, triol |
| (f) | — | 7 keto-5- androstene-3β, 17β, diol |
| (g) | — | 5-androstene-3β, 7α, 17β, triol |
| (h) | — | 5-androstene-3β, 17β, diol-3-sulfate |
| (i) | Testosterone | 17β-Hydroxy-4-androstene-3one |
| (j) | Androstenedione | 4-androstene-3,17 dione |
| (k) | Dihydrotestoserone | 17β-Hydroxy-5β androstane-3-one |
| (l) | Androsterone | 3β-Hydroxy-5β androstan-17-one |

DHEA (a) is known to have immune enhancing activity. However, dehydroepiandrosterone sulphate, "(b)" has been found to have no enhancing effect on the immune system. Both 5 androstene-3β, 11β, 17β,-triol and 5 androstene-3β, 16β, 17β,-triol have immunosuppressive effects. Testosterone, "(i)", is known to have an effect on the host immune response, but this effect does not result in protection from lethal infections. The qualitative and quantitative effects of testosterone and the other sex hormones on the immune response are both of a different nature and scope.

EXAMPLE 1

Use of androstenediol (5 androstene-3β, 17β, diol, βAED) results in marked and significant resistance against viral and bacterial infection. Dose curve experiments were conducted in the following manner: βAED and DHEA were administered as a single depo dose of 8.3 mgs AED or 25 mgs. DHEA to SWR/J and C57BL/6J inbred mice. The mice were then challenged with varying amounts of Coxsackievirus B4 (CB4) to determine protective value of the active agents. βAED provided 50% protective dose against coxsackievirus B4, which was as much as 100 times greater than protection provided by DHEA. In addition, to the difference in ED50, the degree of protection against virus mortality achieved with androstenediol was also greater than the one obtained with DHEA injection. The increased protection effected by βAED against virus induced mortality was statistically significantly different that the protection obtained by DHEA ($P<0.05$).

TABLE 1

DHEA AND AED IN SWR/J MICE MORTALITY PER GROUP*

| | | | |
|---|---|---|---|
| CB4 $10^5$ | VIRUS ALONE 1/6 | DHEA 0/6 | AED 0/6 |
| CB4 $10^6$ | VIRUS ALONE 3/6 | DHEA 0/6 | AED 0/6 |
| CB4 $10^7$ | VIRUS ALONE 5/6 | DHEA 1/6 | AED 0/5 |

TABLE 1-continued

DHEA AND AED IN SWR/J MICE MORTALITY PER GROUP*

| CB4 $10^8$ | VIRUS ALONE 4/6 | DHEA 1/6 | AED 0/6 |
| --- | --- | --- | --- |

*No deaths occurred in control groups.
AED versus control p-value = 0.0001.
DHEA versus control p-value = 0.0017.
DHEA versus AED p-value = 0.0588.

As seen from these results, βAED is markedly more efficient than the precursor DHEA in preventing mortality since an effective dose of βAED which is ⅓ or less the dose necessary to obtain an effect with DHEA is effective in achieving protection from mortality. A similar protection from virus mediated mortality was also observed in the inbred C57BL/6J(b) strain. The two inbred mouse strains, the SWR/J and the C57BL/6J, differ in their major histocompatibility haplotypes, which are q and b respectively. These results show that up-regulation of the immune response achieved with βAED in strains of different histocompatibility may be independent of the major histocompatibility genes on chromosome 17.

Recent reports show that the skin may have unique immune functions. J. W. Streilein and R. E. Tigelar, *Photoimmunology*, Parrish et al. eds. (Plenum Publishing, New York, 1983) pp. 95–130. Indeed the skin is known to contain a population of cutaneous immune cells, which include the epidermal Langerhans cells and keratinocytes that produce an epidermal thymocyte-activating factor, similar to IL-1, in the murine system's Thy-1+ dendritic epidermal cell.

EXAMPLE 2

A composition containing 8 mg βAED was administered subcutaneously to outbred ICR mice who were then challenged with a lethal dose of *Streptococcus faecalis* strain X1515.OG1RF. Animals given βAED showed marked resistance to morbidity as evident from reduction in mortality from 57% in animals challenged with bacteria only, to 0% mortality in animals infected and treated with a single subcutaneous (SC) dose of βAED. Moreover, βAED above a certain threshold dose mediates a considerable proliferation of lymphocyte cells in the spleen and thymus, but only in infected animals. Administration of 8 mg/animal βAED without exposure to the virus did not cause proliferation. Histopathological examination of the organs of inbred SWR/J mice infected with virus only and animals treated with βAED only, or βAED treated and virus infected revealed that βAED is effective in protecting from virus-induced myocardiopathy, and pancreopathy. Data presented in Table 2 below, shows that βAED protects the host ICR inbred strain (Inst. of Cancer Research strain now supplied by Holland Sprague Dowley Company) from *S. faecalis*, but at a dose which is ⅓ the dose of DHEA required for the same effect.

TABLE 2

| BAC-TERIUM | AGENT | DOSE mg/ANIMAL | 24 hr. | % MORTALITY |
| --- | --- | --- | --- | --- |
| *S. faecalis* | none | 0 | 4/7 | 8 |
| *S. faecalis* | DHEA | 25 | 0/7 | 0 |
| *S. faecalis* | AED | 8.3 | 0/7 | 0 |

Protection was accomplished in an extremely acute infection where deaths occurred within 24 hours (4/7 deaths in non-treated groups versus 0/7 in the treated). Mice were challenged with a lethal dose of plasmids containing bacterium *S. faecalis* isolate X1515.OG1RF.

EXAMPLE 3

Wells containing monolayered urinary bladder tumor cells were covered with a 50 µmolar solution of either βAED or DHEA overnight before being used in the assay. The results are shown in Table 3 below.

TABLE 3

| WELL | X1515.OG1RF DOSE | No. ADHERED | % ADHERED |
| --- | --- | --- | --- |
| Media | $1.78 \times 10^6$ | $1.77 \times 10^6$ | 99.4 |
| DMSO | $1.78 \times 10^6$ | $1.98 \times 10^6$ | 111.2 |
| DHEA | $1.78 \times 10^6$ | $1.01 \times 10^6$ | 56.7 |
| AED | $1.78 \times 10^6$ | $1.05 \times 10^6$ | 59.0 |

As can be seen from Table 3, both DHEA and βAED inhibit the adherence of the bacteria to human urinary bladder tumor cells. It is believed that βAED and AET have an effect on either membrane fluidity, or on a component which influences adhesion and/or penetration into the cell. Urinary Bladder Tumor cells (EJ6) were analyzed by flow cytometry using the fluorescent probe 1–4, trimethylammonio-phenyl-6 1,3,5 hexatriene (TMA-DPH) as a membrane probe to determine the effects of AED on membrane fluidity.

Result

A. Samples 1 and 2 represent CONTROL cells grown in standard tissue culture media.

B. Samples 3 and 4 represent cells grown in the above control media with 50 µM AED added.

| Sample A 1. | 0.121256 |
| --- | --- |
| Sample A 2. | 0.120548 |
| CONTROL AVERAGE | 0.120902 |
| AED 50 µM 3. | 0.135151 |
| AED 50 µM 4. | 0.142453 |
| TEST AVERAGE | 0.138802 |

The difference of 0.017899 between the control and βAED-treated cells is significant and demonstrates that βAED caused a significant change in cell membrane adhesion. It may be that an increase in cell membrane rigidity (decrease fluidity) influences adherence.

EXAMPLE 4

Cell culture media was inoculated with $4 \times 10^7$ Hela cells. DHEA was added to a concentration 50 µM and βAED was added to a concentration of 50 µM. The cell culture exposed to DHEA showed a two-fold decrease in cell number. The cell culture exposed to the βAED, the control, and the culture exposed to the carrier alone showed a two fold increase or no change in the number of viable cells. These observations indicate βAED lacks deleterious effects of DHEA during the initial phase of cell response. Neither DHEA nor βAED had an effect on the number of virus infectious particles in vitro.

EXAMPLE 5

Mice were injected with 8 mg βAED or 25 mg DHEA subcutaneously. The mice were then infected with Coxsackievirus B4, $10^5$ particles. The mice were sacrificed after 7 days. The spleen lymphocytes were removed and stimulated with Concavalin A, 5 μg/ml in vitro. Stimulation was measured by $^3$H-thymidine incorporation method. The βAED had a profound effect on the proliferation of spleen lymphocytes with as much as 6.6 fold greater proliferation evidenced. The data also indicates that, during the initial phase following administration of the steroid DHEA results in some suppression of the immune system.

The results described above indicate clearly the advantage of using βAED or βAET rather than DHEA to increase immune response to infections, since the initial immune suppression or toxicity that precedes the immune up-regulation that is seen in treatment with DHEA is avoided. Hence, therapy with βAED and βAET, rather than DHEA is preferred to improve immune response to infectious organisms.

The only change in structure between DHEA and AED is a reduction of the keto group at the 17 position to a β hydroxyl group. The AET which has the hydrogen at the 7 position replaced with a B hydroxyl group is produced by a metabolic pathway in the skin. In other words, βAET is a downstream product of metabolic pathway from DHEA in the skin. The βAET appears to be the most effective compound for effecting immune up-regulation and protection from untoward effects of stress, chemotherapy, and irradiation.

PREPARATORY METHOD #1

An important aspect of the invention is the preparation of sterio-specific βAET for use as a medicinal. The synthesis was accomplished using the 7-oxo-3β, 17β acetoxyandrost-5-ene as a starting material.

SYNTHESIS OF 3β,7β, 17β-TRIHYDROXYANDROST-5-ENE(I) and 3β, 7α, 17β-TRIHYDROXYANDROST-5-ENE(II)

Chromic oxide oxidation of 3β,17β-diacetoxyandrost-5-ene in glacial acetic acid gave 3β,17β-diacetoxyandrost-5en-7-one, (III), the intermediate to (I) or (II).

Aluminum isopropoxide reduction of (III) in isopropanol gave (I). lithium tri (sec-butyl) borohydride reduction of (III) in tetrahydrofuran yielded (II).

PREPARATION OF 3β,17β-DIACETOXYANDROST-5-EN-7-0NE(III)

37.4 g(0.1 mol) 3β,17β-diacetoxyandrost-5-ene (Steraloids A7850) in 400 ml glacial acetic acid was reacted with 30.06 g (0.3 mol) chromium(VI) oxide (Aldrich 23,265-3) dissolved in 20 ml H20 and 20 ml glacial acetic acid. The $CrO_3$ solution was added drop-wise to the 3β,17β-diacetoxyandrost-5-ene solution while maintaining the temperature at 55° C. for 4 hours. In order to decompose any unreacted $CrO_3$, methanol was added to the reaction mixture followed by aqueous salt solution and ether. Evaporation of the ether yielded 7.8 g(20% yield) of crude III,(details are given in lab book #1, pp. 10–16). Crystallization from 95% EtOH yielded (III) m.p. 214°–215° C., DSC peak 191°–224° C., max at 220° C. Lit.,[1] m.p. 218°–219° C., Lit.,[2] m.p. 224°– 225° C. (from methanol).

1. Adolf Butenandt et al. Ber. 71B, 1316–22(1938).
2. Anthony J. Pearson et al., J. Chem. Soc. Perkin Trans. I, 267-273(1985).

Normal phase tlc: EtOAC-cyclohexane-EtOH (45:45:10), Rf=0.86. IR bands (cm−1: 1737,1666 (Lit.,[2] 1728,1668). $^1$H NMR (CDC13),(d), ppm: 0.81(s,3H), 1.25 (s,3H, 2.02(s, 6H), 2.25(m,H at C-4), 2.5(m,H at C-8),4.6(t,H at C-17), 4.7(m,H at C-3), 5.72(s,1H); (Lit.,[2] 0.80(s,3H), 1.20(s,3H), 2.03 (s,6H), 4.62(m,1H), 5.71(g,1H).) Reverse phase 1 c/ms (fast atom bombardment detection) detected m/z 389(M+HJ' ion in the major lc peak,(Lit.,[2] m/z 388(M). Tentative C-13 nmr, (d), ppm assignments (CDC13) are:

2. Anthony J. Pearson et al., J. Chem. Soc. Perkin Trans. I, 267-273(1985).

| Carbon | 1 | 2 | 3 | 4 | 5 | 6 | 7 | 8 |
|---|---|---|---|---|---|---|---|---|
| ppm | 38.35 | 35.74 | 72.04 | 43.03 | 164.22 | 126.44 | 201.18 | 65.82 |
| Carbon | 9 | 10 | 11 | 12 | 13 | 14 | 15 | 16 |
| ppm | 49.69 | 37.76 | 27.26 | 35.95 | 44.72 | 44.95 | 25.83 | 27.55 |
| Carbon | 17 | 18 | 19 | 20 | 21 | 22 | 23 | |
| ppm | 81.90 | 12.05 | 20.67 | 171.14 | 21.24 | 170.23 | 21.17 | |

PREPARATION OF 3β,7β,17β-TRIHYDROXYANDROST-5-ENE(I)

3β,17β-diacetoxyandrost-5-en-7-one was subjected to reduction by aluminum isopropoxide in isopropanol to give 3β,7β,7β-trihydroxyandrost-5-ene.

PREPARATION OF 3β,7α,17β-TRIHYDROXYANDROST-5-ENE(II)

5.1 ml(5.1 mmol) lithium tri(sec-butyl)borohydride (Aldrich L-Selectride) in tetrahydrofuran was rapidly added to 499 mg(1.28 mmol) of 3β,17β-diacetoxyandrost-5-en-7-one in 15 ml of freshly distilled tetrahydrofuran under nitrogen while stirring for 1.5 hours at ice-bath temperature. 0.9 g KOH in 15 ml methanol was added, reaction mixture refluxed for 0.5 hours, and then added 37.5 ml of 10% NaCl solution. After cooling in freezer(−20°), crystals formed which were filtered to yield 123.6 mg (19%) (II), m.p. 239°–45° C. Crystallization from methanol yielded (II), m.p. 249.5°–253° C. $^1$H nmr (CD(OD)$_3$), (d),ppm: 0.75(s,3H), 1.01(s,3H), 3.1(m,1H), 3.6(t,1H), 3.7(d,1H), 5.50 (d,1H).

Tentative C-13 nmr, (d) ,ppm assignments (CD(OD)3) are:

| Carbon | 1 | 2 | 3 | 4 | 5 | 6 | 7 | 8 |
|---|---|---|---|---|---|---|---|---|
| ppm | 37.49 | 32.12 | 72.01 | 42.91 | 146.75 | 124.88 | 65.46 | 39.09 |
| Carbon | 9 | 10 | 11 | 12 | 13 | 14 | 15 | 16 |
| ppm | 43.58 | 38.55 | 21.49 | 30.65 | 93.65 | 45.35 | 38.13 | 42.57 |
| Carbon | 17 | 18 | 19 | | | | | |
| ppm | 82.30 | 11.57 | 19.53 | | | | | |

DISCUSSION

Stereochemistry was assigned to 3β,7β,17β-trihydroxyandrost- 5ene(I) and 3B,7α,17β-trihydroxyandrost-5-ene(II) by comparison with cholest-5-ene-3β,7β-diol and cholest-5-ene- 3β,7α-diol proton nmr(Lit.[3]). L-Selectride reduction of (III) to produce (II) was carried out using the same reaction conditions given by Morisaki for the preparation of 7α-hydroxycholesterol [4]. Carbon-13 resonances for stereoisomers (I) and (II) are shown. (Multiplicities (ppm))

3. Leland L. Smith et al., J.Org. Chem.,Vol.38, No.1, 119–123 (1973).
4. Masuo Morisaki et al., Chem. Pharm. Bull. 35(5)1847–1852, (1987)

| ISOMER(II) | | ISOMER(I) | |
|---|---|---|---|
| 1 | 37.19 | T | 37.77 |
| 2 | 32.12 | T | 32.30 |
| 3 | 72.01 | D | 72.12 |
| 4 | 42.91 | T | 41.24 |
| 5 | 146.75 | * | 144.10 |
| 6 | 121.88 | D | 127.43 |
| 7 | 65.46 | D | 74.00 |
| 8 | 39.09 | D | 38.29 |
| 9 | 43.58 | D | 50.08 |
| 10 | 38.55 | * | 37.73 |
| 11 | 21.49 | T | 21.90 |
| 12 | 30.65 | T | 30.86 |
| 13 | 43.65 | * | 44.27 |
| 14 | 45.35 | D | 52. 31 |
| 15 | 38.31 | T | 26.60 |
| 16 | 42.57 | T | 42.57 |
| 17 | 82.30 | D | 82. 30 |
| 18 | 11.57 | Q | 11.57 |
| 19 | 19.53 | Q | 19.53 |

Q = quartet, T = triplet, D = doublet and * = quaternary C
(ISOMER II, 7-OH axial)   (ISOMER I 7-OH equatorial)

PREPARATORY METHOD #2

A second method of preparing the α and β isomers of AET has been developed. The process uses, as a starting material, 3β, 17β diacetoxyandrost-5-ene, a commercially available reagent (Stereloids A7850). This compound is oxidized with chromium hexacarbonyl (Cr(Co)$_6$) to form 3β. 17β-diacetoxyandrost-5-en-7-one as described by Pearson (Pearson, et al., *J. Chem Soc. Perkin. Trans.* 1, 1985, 267.) The enone formed was then reduced with triisobutylaluminum (TIBA) to give the acetylated 7α-hydroxy (3a) or 7β-hydroxy (3b) product depending on the solvent used.

PREPARATION OF 3β, 7α. 17β-TRIHYDROXYANDOST-5-ENE

A solution of 3β,17β-diacetoxyandrost-5-en-7-one (0.4991 g., 1.285 mmol) and tetrahydrofuran (20 mL, dried over MgSO$_4$) were mixed under a nitrogen atmosphere. TIBA (2 mL, 2 mmol, in 1M toluene) was added dropwise by syringe The solution was stirred at room temperature for about 7 hours. The reaction was terminated by the addition of ethyl acetate (1.4 mL), the methanol (10 mL), and finally, by addition of 10 mL of 50% acetic acid. This solution was added to 100 mL water and extracted with ethyl acetate (3 times with 50 mL.) The organic layers were combined and then washed with saturated sodium bicarbonate solution (50 mL), saturated sodium chloride solution (2 times with 50 mL) and water (50 mL). The organic layer was then dried over magnesium sulfate and the solvent removed by rotary evaporation to yield >96% crude product. $^1$H NMR indicated that the crude product contained 3β,17β-diacetoxyandrost-5-en-7-one (starting material), 65% and 3β,17β-diacetoxy-7α-hydroxyandrost-5-ene, 35%.

PREPARATION OF 3β,7β,17β-TRIHYDROXYANDROST-5-ENE

A solution of 3β,17β diacetoxyandrost-5-en-7-one (0.9581 g, 2.466 mmol) and pentane (30 mL), dried over MgSO$_4$) were mixed under a nitrogen atmosphere. TIBA (9.5 mL, 9.5 mmol, 1M in toluene) was then added dropwise by syringe. The solution was stirred at room temperature for about 1 hour. The reaction was terminated by the addition of diluted hydrochloric acid (approximately 5 mL). This solution was added to water (100 mL) and extracted with ethyl acetate (3 times with 50 mL). The organic layers were combined and then washed several times with saturated sodium bicarbonate solution (50 ml), saturated sodium chloride solution (two times with 50 mL,) and water (50 mL). The organic layer was dried over magnesium sulfate and the solvent removed by rotary evaporation to yield 86% crude product. $^1$H NMR indicated that the crude product contained 3β,17β,-diacetoxy-7-β -hydroxyandrost-5-en-7-one (86%) and 3β,17β-diacetoxy-7-α -hydroxyandrost-5-ene.

In both of the above instances, the final products were reduced in accord with preparatory method #1.

The compositions of the invention containing βAED and βAET, are useful in treatment any condition wherein a condition related to immune response is present including diabetes mellitus, chronic fatigue syndrome, stress, chemotherapy, and exposure to irradiation. One of the more depressing results of many of these conditions that involve aberrations of the immune response includes alopecia. The compounds of the invention are effective for treating the alopecia resulting from such aberrations of immune response, including effects of chemotherapy and irradiation. In alopecia, the αAET should be of considerable benefit for use in treatment. The compositions of both βAED and βAET are useful in overcoming other untoward effects of immune suppression arising in these conditions.

EXAMPLE 6

SWR/J inbred mice were injected with single depo doses of 0.5, 2.0, 4.0 and 8.0 mg/animal of βAED, then challenged with $10^7$ PFU Coxsackievirus B4. The results are shown below:

| AED dose, mg/animal | % cumulative survival |
|---|---|
| 0 | 17 |
| 0.5 | 83 |
| 2 | 100 |
| 4 | 100 |
| 8 | 100 |

Based on these results, the theoretical dose (extrapolated) of βAED necessary to achieve 50% protection from infection with $10^7$ PFU of CB4 is 0.25 mg/animal.

The example demonstrates that βAED is 50 to 100 times more potent than DHEA for protection from Coxsackievirus B4.

EXAMPLE 7

In an attempt to evaluate effect of βAED on pathologies of the heart and pancreas in infected mammals, three groups of inbred SWR/J mice were compared. The groups studied included animals infected with virus only, animals treated with βAED only, and animals infected with virus and protected with βAED. The comparison revealed the following:

| | Heart | Pancreas |
|---|---|---|
| AED | unremarkable | unremarkable |
| VIRUS | focal areas of multiple necrosis with substantial | severe necrosis (Pancreopathy) |

-continued

|  | Heart | Pancreas |
|---|---|---|
| AED PLUS virus | myocardial calcification. no evidence of induced myocardiopathy | no evidence of virus induced pancreopathy |

These results demonstrate that βAED given as a single depo dose at 8.0 mg/mouse protected the heart tissue from virus induced myocardiopathy, and also protected the pancreas from virus induced necrosis of this organ. These results show that βAED can be used effectively in the protection from virus-induced cardiovascular and pancreatic disease, in particular myocardiopathies and pancreopathies. Previously there were no effective drugs to protect these organs from virus induced damage.

EXAMPLE 8

Effectiveness of βAED, αAET, and βAET were compared by challenging mice with Coxsackievirus B4, $5.0 \times 10^7$ pfu/animal. The following data represents total cumulative mortality (n/6) at indicated days post infection with virus.

| Treatment Group | Cumulative mortality (Days Post Infection) | | | | | | | |
|---|---|---|---|---|---|---|---|---|
|  | 2 | 4 | 6 | 8 | 10 | 12 | 14 | 16 |
| Virus alone | 0 | 1 | 6 | * | * | * | * | * |
| βAED .5 mg/virus | 0 | 0 | 1 | 1 | 6 | * | * | * |
| αAET .5 mg/virus | 0 | 1 | 4 | 4 | 4 | 4 | 4 | 4 |
| βAET .5 mg/virus | 0 | 0 | 1 | 1 | 2 | 2 | 4 | 4 |

While the αAET appeared to protect two animals from the virus, the initial mortality would indicate that at least in early stages, there is little or no protection from the αAET. Other studies indicate that there is far less protection with αAET than with either βAED or βAET. Clearly, the βAET is the most effective agent for both early and longer term protection. It appears that there is a limited protection attributable to αAET. Therefore, this isomer would not be as beneficial as βAET for effecting enhancement of immune response.

The use of βAED or βAET as active agents to provide regulation of the immune system makes it possible to effectively regulate the host immune response against viral, bacterial and other infections. In the case of virus-induced heart or pancreatic infection where no other antiviral chemotherapeutic modality exists βAED and βAET have value as prophylactic protective agents. The protective value of βAED and βAET is particularly important to patients undergoing surgical procedures or suffering injuries where resistant strains of organisms such as pseudomonas present a serious threat. Examples of such patients are those undergoing bowel surgery or suffering from gunshot wounds of the abdomen. Patients with history of conditions such as rheumatic fever would also benefit from prophylactic use of βAED and βAET. The mode of administration in a particular case will depend on the infectious agent against which protection is sought and the target tissue of the organism. While the administration subcutaneously as a depo is effective against systemic infections as shown by the data presented above, when the compositions are given to assist the body in meeting an infection in a particular tissue, it may be advantageous to administer the active agents to the tissues most affected.

The carrier used in a given instance will depend on the mode of administration. Both AED and AET are lipophilic compounds. They are more soluble than DHEA in water. Solvents for lipophilic steroids are known in the art and would be used as carriers for these compounds. Examples of such carriers are glycols such as polypropylene glycol, polyethylene glycol and cyclodextrins, especially the intrinsically amorphous cyclodextrins. Other vehicles that should be considered include fatty acid esters of polyoxyethylene sorbatan (Tweens) or sorbitan (Spans) to prepare oil-in-water emulsions.

EXAMPLE 9

Capsules of a formulation of AED for oral administration are prepared by containing 15 mg. βAED, 150 mg. starch, and 5 mg. magnesium stearate. The capsules are administered daily or twice a day to achieve a daily dosage of 15 mg. per day.

In the laboratory, βAED was added to the chow of the animals at a rate of 0.4% of the diet. When the animals who had been fed the diet containing βAED were exposed to Coxsackievirus B4 by injection in accord with the teachings of Example 1, the animals who had been fed the βAED survived, while control animals all died.

EXAMPLE 10

A preparation for application to the skin or mucosa may be prepared in the following manner:

| Ingredient | % w/w |
|---|---|
| AED | 0.5% |
| glyceryl monostearate | 3.0% |
| propylene glycol | 13.0% |
| Petrolatum | 83.5% |

When βAED or βAET or their analogues are administered orally, the active agents may be utilized more efficiently if the active agents are protected from destruction and absorption in the upper gastro-intestinal tract. The active agents are most effective when the period of exposure to the mucosa of the intestinal tract is increased. Hence use of capsules containing the active agents in formulations that effect slow release in the intestine are appropriate for treatment of intestinal disorders such as Crohn's disease and colitis. Use of retention enemas for treatment of inflammation of the large bowel is also appropriate.

A formulation for administration as a retention enema may be formulated in the following manner:

EXAMPLE 11

| Ingredient | w/w % |
|---|---|
| βAET | 4% |
| Propylene glycol | 96% |

When the active agent is administered to the mucosa of the oral cavity, it may be administered as a buccal tablet or spray for use in the oral-pharyngeal cavity and the nasal cavities.

The compositions could also be administered to the bronchial tree via inhalation. This means of administration would be particularly useful in treating patients with lung infections or in treating other lung conditions such as black lung disease or emphysema that often are complicated by opportunistic infections. The compositions could be given by aerosol into the trachea or administered in mist along with other agents used in respiration therapy.

The administration of the βAED and βAET to the skin can be accomplished using patches wherein a support is impregnated with the active agent or using implants that provide slow release of the active agents.

Patches for the administration of AET or AED can be formulated as adhesive patches containing the drug. For example, the patch may be a discoid in which a pressure-sensitive silicone adhesive matrix containing the active agent may be covered with a non-permeable backing. The discoid may either contain the active agent in the adhesive or may have attached thereto a support made of material such as polyurethane foam or gauze that will hold the active agent. Before use, the material containing the active agent would be covered to protect the patch.

EXAMPLE 12

A patch composed of trilaminate of an adhesive matrix sandwiched between a non-permeable backing and a protective covering layer is prepared in the following manner:

To a pressure-sensitive silicone adhesive composition BIOPSA™ Q7-2920 (Dow Corning Corp., Midland, Mich., U.S.A.) in cyclohexane (50% w/v) is added sufficient βAED to provide a 0.5% βAED composition. The adhesive is applied to a polyester film to provide in successive layers to provide about 2 mg of active agent per $cm^2$. The film containing the adhesive is then made into patches of 10 $cm^2$. Patches would be covered with a protective layer to be removed before application of the patch. Patches may be prepared containing permeation enhancers such as cyclodextrin, butylated hydroxyanisole, or butylated hydroxytoluene. However, it should be remembered that the active agents of this invention are effective on application to the epidermal tissue. When the patches are to be applied to thin or abraded skin, there is little need to add a permeation enhancer.

Compositions of the invention can be administered as a prophylactic during radiation therapy or chemotherapy or after exposure to irradiation whether the exposure occurs as a result of environmental accident or therapy. Other instances when use of these immune up-regulators would be appropriate is in treatment of burns, hypoplastic and aplastic anemias, diabetes, and in the elderly during epidemics. Their use is also beneficial in preventing or mitigating effects of exposure to dangerous infectious organisms, as was demonstrated by the data related to cardiopathies and pancreopathies. Such use is particularly indicated in populations exposed to organisms that target the immune system, such as HIV infections. In certain instances the compositions taught herein can also be used as immune modulators in the production of blocking antibodies to counteract hypersensitivity reactions.

As indicated previously, patients scheduled to undergo bowel surgery or other "dirty" surgical procedures could receive a dose of βAED or βAET prophylactically. Use of the compositions as taught herein before invasive dental procedures or oral surgery should be considered.

As indicated in the tables and previous discussion, the compositions of the invention can be used to prevent adhesion of bacteria to the tissues. The prevention of cell to cell adhesion resulting from administration of the compositions also has applications for prevention of thrombosis. Compositions of the invention can be administered as a slow drip into blood vessels when prevention of formation of a thrombus is necessary. An example of such use would be a drip into an artery following thrombolectomy or for prevention of cerebral thrombosis. Instillation into the bladder could also be beneficial for prevention or treatment of urinary infection. The administration of the βAED or βAET can be employed as a means of preventing formation of infectious foci.

βAED and βAET are both effective in overcoming effects of ultraviolet depravation. Hence, administration of the compositions to overcome the effects of depression related to light deprivation (usually called seasonal adaptive disorder) is appropriate.

βAED and βAET may be used as adjuncts in vaccination to increase response to an immunogen. Not only will these agents increase response to the vaccine, they will also increase ability to protect against disease before the body has responded with increase in specific antibodies. Such use is particularly appropriate in instances where inhibition of immune response can be a complicating factor as is the case in patients suffering from, for example, malignancies, AIDS, or environmental factors such as exposure to pesticides. It is, of course, understood that use as adjunct to vaccination would be appropriate in vertebrates other than man, including vaccination of pets, dairy animals, meat-producing animals, fish, and chickens. Chickens are particularly prone to develop infectious diseases when living in confined conditions. Coccidiosis, Salmonella infections, viral infections, including those giving rise to malignancies such as leukemia and sarcoma (caused by a retrovirus) are particularly common among chickens grown under modern commercial conditions. The active agents of the invention may be given by any means that results in contact of the agent with tissue of ectodermal origin.

The effect of Coxsackievirus on humans has been noted previously. The value of avoiding such effects, especially in children, is clear. Effects of other viruses such as chickenpox-herpes zoster is considered an important cause of debilitating illness in the elderly. Furthermore, chickenpox in susceptible adults often causes severe illness. In children, chicken pox can cause death when the child is subjected to immuno suppressive therapy or is genetically immune deficient. βAED and βAET a useful for prophylatic treatment of susceptible persons who have been exposed to infection. Finally, the protection of the fetus and newborn from HSV infection is a very important application of the invention. βAED and βAET can be administered during the third trimester to HSV-infected women as a means of protecting the newborn.

In vitro, these compounds can be used in commercial setting to induce lymphocyte proliferation. The use of βAED and βAET would increase yield of products of such proliferation in tissue culture. In the clinical setting, βAED and βAET can be given to effectively enhance patients' ability to combat infections. Patient lymphocytes may be withdrawn, reproduced in vitro in media containing βAED or βAET to increase proliferation of lymphocytes, and the lymphocytes so primed for response could then be reintroduced into the patient. In cases such as malignancy or other cellular disease, the malfunctioning cells can be inactivated by known means before proliferation in growth media.

The compositions of the invention may also be used prophylactically to protect animals from the consequences of infection by pathogenic organisms. It is known that under the stress of shipment to market animals often become susceptible to infections that are not ordinarily serious, but that can cause the animals to loss much weight en route to the packing house. Such loss may be avoided by administration βAED and βAET and analogues disclosed herein. The active agents can be given by patch, injection, or in feed. Because the active agents are most effective when the period of exposure to the tissue of ectodermal origin is extended, when the active agents are administered through the GI tract, compositions should be modified to extend the period of exposure of the active agent to the intestinal mucosa and to protect the agents from destruction in the upper GI tract. Hence, use of capsules that effect slow release in the intestine is appropriate. The capsules may be placed in baits for administration to animals. To treat infections of the large bowel, the active agents may be given by retention enema.

βAED and βAET may be administered to the mucosa of oral, pharyngeal, and nasal cavity by tablet, a lozenge, by administration as a spray for use in the oral-pharyngeal cavity, or as a nasal spray.

Administration to the skin may be accomplished using patches wherein a support to be applied to the skin is impregnated with the active agent. If the host is a mammal or bird, it may be necessary to shave or pluck the region to which the patch is applied.

A preferred method of administration is by subcutaneous injection as a depo. The method is particularly appropriate for administration of the active agents to mammals, since subcutaneous injection is easily performed and the effect is relatively long lasting.

βAED and βAET are already present in the body as natural components. They do not pose a serious toxic problem at levels known to be safe; they appear to be chemically quite stable.

The dosages used will depend on the size and condition of the host. Test data indicated in this application was obtained in small animals. In larger adult mammals daily dosage of 0.2 to 30 mg/da. of AED is a preferred dosage. For AET the preferred dosage is usually in the range of 0.001 to 20 mg/da, with 0.001 to 1 mg/da. being the more preferred dosage. However, the dosage will vary depending on the route of administration. Subcutaneous, inhalation and intrathecal administration are methods that would require lower dosages of the active agents.

It is, of course, understood that analogues of βAED and βAET having protective groups can be administered to the host as a means of delivering βAED or βAET to target tissues. Acylation is a preferred method of protecting the compounds. Acylated compounds wherein $R_1$ is $COR_2$ are also appropriate compounds for use as starting material from which to make βAED and βAET.

The active agents, βAED and βAET, can be given in conjunction with other active agents which may be given simultaneously or may be incorporated in compositions containing βAED or βAET. βAED and βAET can be given with anti-infective agents such as antibiotics, antiviral agents, anti-fungals, antiparasitic agent to potentiate the activity of these drugs by up-regulating protective immune response. Antiviral agents include, for example, Dideoxyinosine, AZT, acyclovir, etc. Other active agents that may be combined with the AED and AET include antiallergic medications such as epinephrine.

Finally, medicinal compositions containing βAED and βAET are particularly valuable for use in combating viral infections in patients who have suffered from infections exacerbated by immuno-suppressive therapy. One of the major complications in patients with tissue transplants is the opportunistic infection with viruses that ordinarily do not cause serious disease symptoms. Use of the compositions of the invention, which result in rapid protective regulation of the immune response, allows the medical team to place the patient on "see-saw" therapy to avoid transplant rejection while regulating the immune response to avoid overwhelming infection.

I claim:

1. A method of preventing or ameliorating untoward effects of chemotherapy or irradiation therapy in a mammal in need of such treatment by administration of an effective amount of a composition containing as an active agent 5-androstene 3β,17β diol (βAED) or 5-androstene 3β,7β, 17β triol (βAET) or at least one compound of the formula:

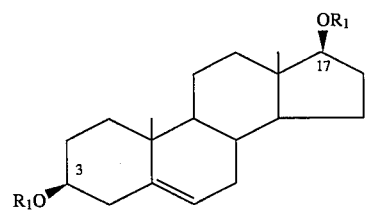

and

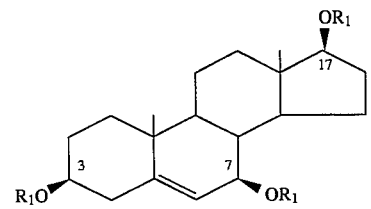

wherein $R_1$ may be H, alkenyl of 2–8 carbons, alkyl of 1–8 carbons, phenylalkyl of 1–4 carbons, phenyl or $COR_2$, wherein $R_2$ is H; alkyl of 1–8 carbons, alkenyl of 2–8 carbons, phenylalkyl wherein the alkyl has 1–4 carbons or phenyl with the proviso that at least one of the $R_1$'s is not H, and any phenyl moiety may have up to three substituents chosen from among hydroxy, carboxy of 1–4 carbons, halo, alkoxy of 1–4 carbons, alkyl of 1–4 carbons, or alkenyl of 2–4 carbons and wherein any alkyl may be a straight chain, branched chain, or the alkyl may be wholly or partially cyclized in a pharmaceutically acceptable carrier.

2. A method of claim 1 wherein the active agent used is βAET.

3. A method of claim 1 wherein the active agent is βAED.

4. A method of claim 1 wherein the active agent is administered through a patch or an implant.

5. A method of claim 1 wherein the composition is administered subcutaneously, intradermally, or by topical application.

6. A method of claim 1 wherein the composition is administered intrathecally.

7. A method of claim 4 wherein the composition is administered as a patch.

8. A method of claim 1 wherein the composition is administered intranasally.

9. A method of claim 1 wherein the composition is administered by mouth.

10. A composition of matter comprising as an active agent an immune-enhancing amount of 5-androstene 3β,7β,17β triol (βAET) in a pharmaceutically acceptable carrier.

11. A composition of claim 10 containing a glycol.

12. A composition of claim 10 wherein the active agent is attached to a support.

13. A composition of claim 12 wherein the composition is a patch.

14. A composition of claim 10 in a closed container.

15. A composition of claim 10 for oral administration in capsule form.

16. A composition of claim 10 adapted for implantation.

* * * * *